United States Patent [19]

Mane et al.

[11] Patent Number: 5,861,286
[45] Date of Patent: Jan. 19, 1999

[54] BIOCHEMICAL PROCESS FOR PREPARING AROMATIC SUBSTANCES

[75] Inventors: Jean Mane, Grasse; Joseph Zucca, Antibes, both of France

[73] Assignee: V. Mane Fils, France

[21] Appl. No.: 860,876

[22] PCT Filed: Jan. 18, 1996

[86] PCT No.: PCT/FR96/00082

§ 371 Date: Sep. 25, 1997

§ 102(e) Date: Sep. 25, 1997

[87] PCT Pub. No.: WO96/22381

PCT Pub. Date: Jul. 25, 1996

[30] Foreign Application Priority Data

Jan. 19, 1995 [FR] France .................................. 95-00581

[51] Int. Cl.⁶ .............................. C12P 7/24; C12P 19/44; C07C 47/58; C07H 15/203

[52] U.S. Cl. ........................... 435/74; 435/147; 435/189; 568/426; 568/431; 568/432; 568/436; 568/437; 568/438

[58] Field of Search .............................. 435/74, 147, 156, 435/189; 568/426, 438, 431, 432, 436, 437

[56] References Cited

PUBLICATIONS

Derwent Abstract 93–316614/40 JP05227980 (Sept. 07, 1993) Takasago Peerfumery Co. Ltd. Sep. 7, 1993.

*Primary Examiner*—Herbert J. Lilling
*Attorney, Agent, or Firm*—Larson & Taylor

[57] ABSTRACT

The present invention relates to a process for the preparation of aromatic substances having formula (I), characterized in that a substrate having formula (II) is subjected to an oxydation in the presence of at least one protein and at least one metal ion, formula wherein $R_1$ may be a radical —H, —$CH_3$, —$CH_2OH$, —CHO, —COOH, —$OCH_3$, or —COO—CH(COOH)—$CH_2$—$C_6H_3(OH)_2$; $R_2$ may be a radical —H, —OH, or —$OCH_3$; $R_3$ may be a radical —H, —OH, —$OCH_3$, or O-glucosid; $R_4$ may be a radical —H, —OH, or —$OCH_3$.

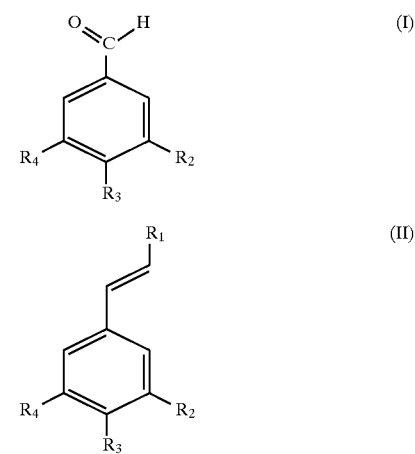

18 Claims, No Drawings

BIOCHEMICAL PROCESS FOR PREPARING AROMATIC SUBSTANCES

The invention relates to a biochemical process for the preparation of certain aromatic substances.

The term aromatic substances means natural aldehydes having an aromatic interest, that is, a perfume and/or a flavour suitable for the use thereof in the food, pharmaceutical or perfume industries.

Various processes for the preparation of natural aldehydes have already been described. For example:

U.S. Pat. No. 4,617,419 describes a process for the preparation of benzaldehyde and acetaldehyde by means of a "retro-aldol" reaction, phenyl aldehydes are prepared by an enzyme process in European patent application no. 542 348, U.S. Pat. Nos. 5,017,388, 5,128,253 and European patent application no. 453 368 describe processes for the preparation of vanillin involving the use of microorganisms, U.S. Pat. No. 5,057,424 describes a process for the preparation of aromatic compositions of vanilla by means of vegetable cells.

Said processes require, however, the use of specific and expensive compounds or products which have to be used under relatively stringent conditions.

The object of the present invention is to overcome the disadvantages of the art and allows the preparation of aromatic substances by means of compounds which are easy to procure, inexpensive and under reaction conditions which are simple to achieve.

To its credit, the applicant has, in fact, established that it was possible to prepare aromatic substances having the formula:

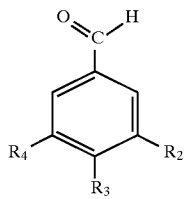

by submitting to oxidation in the presence of at least one protein and at least one metal ion, a substrate corresponding to the formula

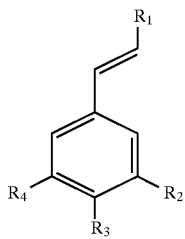

wherein $R_1$ may be a radical —H, —$CH_3$, —$CH_2OH$, —CHO, —COOH, —$OCH_3$, or —COO—CH(COOH)—$CH_2$—$C_6H_3(OH)_2$, $R_2$ may be a radical —H, —OH, or —$OCH_3$, $R_3$ may be a radical —H, —OH, —$OCH_3$, or 0-glucoside, $R_4$ may be a radical —H, —OH, or —$OCH_3$.

With regard to the radical $R_3$, the glucoside of the radical 0-glucoside is chosen from the group comprising the glucopyranoside alone or attached to an oside such as glucopyranoside, rhamnopyranoside, arabinopyranoside.

Advantageously, the aromatic substances according to the invention belong to the group comprising vanillin, benzaldehyde, anisaldehyde and protocatechualdehyde.

The protein used in the process according to the invention may be chosen from:

the metalloproteins, that is:

proteins or enzymes having a heme structure; these may include myoglobin, haemoglobin, cytochromes (c, P450 . . . ) and numerous oxydoreductases such as peroxydase, catalase, cytochrome oxydase, or dehydrogenases such as alcohol dehydrogenase, or oxygenases, proteins or enzymes joined to a metal ion, which may include ferritin and ferredoxin and certain dioxygenases, proteins known as "simple" proteins, the action of which, within the context of the present invention, must be completed by a metal ion not contained in their structure, this metal ion being either in the free form or in the complexed form (for example, complexed with porphyrins or protoporphyrins); these may include gelatin, casein, bovine serum albumin.

Whatever the protein used in the process according to the invention, the metal ion in the free or complexed form is chosen from the group comprising iron, cobalt, copper, magnesium, manganese, and zinc.

Advantageously, several proteins and several metal ions in the free or complexed form, may be used simultaneously in the process according to the invention. Indeed, it was observed that the yields obtained were all the higher if they resulted from the use of the combination of at least two of the following compounds: a "simple" protein, a metalloprotein, a metal ion, a protoporphyrin, a porphyrin.

The process according to the invention has, in particular, the advantage that it may be used with compounds that are inexpensive and easy to procure. Moreover, the reaction conditions do not require any particular precautions as regards sterility or regulation of the reaction medium.

According to an advantageous embodiment of the process according to the invention, the metal ion in whatever form it may take is used in a quantity of 0.0005 to 0.2% by weight with respect to the substrate.

Advantageously, the substrates subjected to the joint action of a protein and a metal ion are chosen from the group comprising isoeugenol, eugenol, cinnamaldehyde, anethole and rosmarinic acid.

The proteins used in the process according to the invention may be used in the purified or unpurified form. In an unpurified form, said proteins may be used by way of compositions containing them such as a suspension of microbial cells, a ground preparation of cells, tissues or organs of vegetable or animal origin, or of a protein preconcentrate of said compositions known as an acetone fraction. The following may be mentioned by way of example:

bacterial cells of yeast or mould, ground vegetable matter such as aubergine fruits, tomato fruits, spinach leaves or radish tops animal extracts such as fresh blood, dried blood or liver cells.

According to one advantageous embodiment of the process according to the invention, the protein in whatever form it may take is used in a quantity of 0.01 to 20% by weight with respect to the substrate, preferably in a quantity of 0.1 to 5% by weight with respect to the substrate.

The process according to the invention may be used in water or in an aqueous medium buffered with the aid of a phosphate, citrate, borate or phosphate-citrate-borate buffer, whereby the pH of the reaction must be between 2 and 10.

Advantageously, in the event that the substrate is isoeugenol, anethole or cinnamaldehyde, the pH is preferably between 4 and 9 and more preferably between 5 and 7; in the event that the substrate is eugenol, the pH is preferably between 2 and 7 and more preferably between 2.5 and 4.5.

The process according to the invention may also be used in a non-aqueous medium such as in one or more organic solvents chosen from: hexane, cyclohexane, methyl cyclohexane, dichloroethane, dichloromethane.

Moreover, in the event that the substrate is eugenol, and because of the very great reactivity of its SH groups, the addition of a sulfhydryl compound may be favourable. Said compound may be chosen from the group comprising cysteine, glutathione, dithiothreitol, dithioerythritol.

According to other advantageous characteristics of the invention:

the temperature of the reaction medium is between 15° and 50° C. and preferably between 25° and 40° C., the aeration of the reaction medium must allow the supply of at least one mole of oxygen per mole of substrate to be oxidised; consequently, the reaction can be carried out at atmospheric pressure but may give rise to improved yields if the reaction medium is enriched with air or oxygen, for example, by simple bubbling; the reaction can also be carried out under a pressure between $10^3$ and $10^7$ pascals, the reaction medium is subjected to vigorous agitation which may be between 150 and 250 rpm on an agitated table and between 100 and 1000 rpm in a stirred reactor, the reaction time is between 2 hours and 5 days, the aromatic substances prepared are isolated from the reaction medium by extraction or by distillation.

The invention is not strictly limited to the process described; on the contrary, it includes all the variations thereof.

The examples that follow serve to illustrate the invention; they are not limiting and relate to advantageous embodiments of the invention.

EXAMPLE 1

Preparation of Vanillin

A basic reaction medium is prepared to serve as a reference comprising:

20 g of borate buffer, 0.1M, pH 6.5, 800 mg of isoeugenol and 50 mg of Tween 80.

A reaction medium according to the invention is also prepared and comprises, apart from the basic reaction medium, purified haemoglobin.

The reaction media are incubated at 28° C. for 3 days in flasks placed on an agitated table at 175 rpm.

The results obtained are given in Table I.

TABLE I

| Composition of the reaction medium | Vanillin obtained in g/l | Yield |
|---|---|---|
| Basic medium (reference) | 1.27 | 100% |
| Basic medium + purified haemoglobin (20 mg) | 1.55 | 120% |

It can be seen very clearly that the addition of purified haemoglobin improves appreciably the yield in which vanillin is obtained.

EXAMPLE 2

Preparation of Vanillin

The basic reaction medium serving as a reference is the same as that of Example 1.

Several reaction media according to the invention are prepared and comprise, apart from the basic reaction medium described in Example 1, at least one of the following compounds in the quantity indicated:

gelatin, iron in the form of $FeCl_2$, protoporphyrin IX.

The reaction conditions are identical to those given in Example 1.

The results obtained are summarised in Table II.

TABLE II

| Composition of the reaction medium | Vanillin obtained in g/l | Yield |
|---|---|---|
| Basic medium (reference) | 0.93 | 100% |
| Basic medium + gelatin (20 mg) | 0.6 | 64.50% |
| Basic medium + iron (0.1 mg) | 0.85 | 91.40% |
| Basic medium + gelatin (20 mg) + iron (0.1 mg) | 1.35 | 145% |
| Basic medium + gelatin (20 mg) + protoporphyrin (20 mg) + iron (0.025 mg) | 4.59 | 493% |
| Basic medium + gelatin (20 mg) + protoporphyrin (20 mg) + iron (0.125 mg) | 5.29 | 568% |

Whereas the yield obtained with the basic medium+ gelatin or the basic medium+iron is lower than that obtained with the basic medium alone (simple observation), the combination of gelatin+iron allows the quantity of vanillin obtained to be increased considerably, particularly if protoporphyrin is present in the medium and the quantity of iron in the medium is high.

EXAMPLE 3

Preparation of Vanillin

The basic reaction medium serving as a reference is the same as the one in Example 1.

Several reaction media according to the invention are prepared and comprise, apart from the basic reaction medium described in Example 1, at least one of the following compounds in the quantity indicated:

purified haemoglobin, iron in the form of $FeCl_2$, protoporphyrin IX.

The reaction conditions are identical to those given in Example 1.

The results obtained are given in Table III.

TABLE III

| Composition of the reaction medium | Vanillin obtained in g/l | Yield |
|---|---|---|
| Basic medium (reference) | 1.15 | 100% |
| Basic medium + purified haemoglobin (20 mg) | 1.72 | 149% |
| Basic medium + purified haemoglobin (20 mg) + protoporphyrin (20 mg) + iron (0.025 mg) | 3.56 | 309% |

TABLE III-continued

| Composition of the reaction medium | Vanillin obtained in g/l | Yield |
|---|---|---|
| Basic medium + purified haemoglobin (20 mg) + protoporphyrin (20 mg) + iron (0.125 mg) | 5.07 | 440% |

The effect of haemoglobin on the yield is increased by the presence of protoporphyrin and iron, all the more so if the quantity of the latter is high.

EXAMPLE 4

Preparation of Vanillin

In a stirred reactor, a basic reaction medium is prepared to serve as a reference comprising:

2 l of borate buffer, 0.1M, pH 6.5, 80 g of isoeugenol and 500 mg of Tween 80.

Two reaction media according to the invention are also prepared and comprise, apart from the basic reaction medium, respectively 1 g of purified haemoglobin and 1 g of dried blood.

The reaction media are incubated at 30° C. for 24 hours in an agitated medium at 600 rpm, under a pressure of $4.10^4$ pascals of oxygen.

The results obtained are summarised in Table IV.

TABLE IV

| Composition of the reaction medium | Vanillin obtained in g/l | Yield |
|---|---|---|
| Basic medium (reference) | 1.75 | 100% |
| Basic medium + purified haemoglobin (1 g) | 3.45 | 196% |
| Basic medium + dried blood (1 g) | 4.25 | 243% |

Dried blood, the composition of which comprises, apart from haemoglobin, plasma proteins (such as albumin and globulins) and iron, makes it possible to obtain even better results than with purified haemoglobin.

EXAMPLE 5

Preparation of Vanillin

In a stirred reactor, a basic reaction medium is prepared to serve as a reference comprising:

2 l of borate buffer, 0.1M, pH 6.5, 100 g of isoeugenol and 500 mg of Tween 80.

A reaction medium according to the invention is also prepared and comprises, apart from the basic reaction medium, 2 g of purified haemoglobin.

The reaction media are incubated at 30° C. for 24 hours in an agitated medium at 600 rpm under a pressure of $5.10^4$ pascals of oxygen.

The results obtained are given in Table V.

TABLE V

| Composition of the reaction medium | Vanillin obtained in g/l | Yield |
|---|---|---|
| Basic medium (reference) | 1.75 | 100% |
| Basic medium + purified haemoglobin (2 g) | 8.4 | 480% |

These results confirm the results obtained in the previous examples.

EXAMPLE 6

Preparation of Vanillin

Two identical basic reaction media are prepared comprising:

25 g of borate buffer, 0.1M, pH 6.5, 400 mg of isoeugenol and 50 mg of Tween 80.

To one of them, regarded as the reference medium, are added 25 g of finely ground aubergine fruit which has undergone a heat treatment beforehand at 110° C. for 15 minutes.

The other medium is supplemented with 25 g of finely ground aubergine fruit which has not been heat-treated (fresh fruit).

It is known that the whole aubergine fruit contains proteins in a quantity of 1 g per 100 g of aubergine. Thus, 25 g of aubergine contain about 250 mg of proteins (including certain oxidative enzyme activities) and about 0.075 mg of iron and 3.75 mg of magnesium.

The two media are incubated at 28° C. for 3 days in flasks placed on an agitated table at 175 rpm.

The results obtained are given in Table VI.

TABLE VI

| Composition of the reaction medium | Vanillin obtained in mg/l | Yield |
|---|---|---|
| Basic reference medium | 700 | 100% |
| Basic medium + fresh fruit (25 g) | 1750 | 250% |

This shows that the ground vegetable matter in particular makes it possible to obtain excellent results within the context of the invention.

EXAMPLE 7

Preparation of Vanillin

A basic reaction medium is prepared to serve as a reference comprising:

20 g of phosphate/citrate/borate buffer, 0.1M, pH 6.5, 800 mg of eugenol and 50 mg of Tween 80.

Two reaction media according to the invention are also prepared and comprise, apart from the basic reaction medium, respectively cysteine and cysteine+purified haemoglobin.

The reaction media are incubated at 30° C. for 2 hours in an agitated medium at 150 rpm under a pressure of $8.10^5$ pascals of oxygen.

The results obtained are given in Table VII.

TABLE VII

| Composition of the reaction medium | Vanillin obtained, in mg/l | Yield |
| --- | --- | --- |
| Basic medium (reference) | 18 | 100% |
| Basic medium + cysteine (0.6 g) | 177 | 983% |
| Basic medium + cysteine (0.6 g) + purified haemoglobin (20 mg) | 703 | 3950% |

The great reactivity of eugenol with respect to cysteine is shown here and the yield of this combination is increased considerably by the addition of purified haemoglobin.

EXAMPLE 8

Preparation of Vanillin

A basic reaction medium is prepared to serve as a reference comprising:

20 g of phosphate/citrate/borate buffer, 0.1M, pH 6.5, 800 mg of eugenol, 50 mg of Tween 80.

A reaction medium according to the invention is also prepared and comprises, apart from the basic reaction medium:

cysteine, gelatin, protoporphyrin IX and iron in the form of $FeSO_4$.

The reaction media are incubated at 30° C. for 2 hours in an agitated medium at 150 rpm under a pressure of $10^5$ pascals of oxygen.

The results obtained are summarised in Table VIII.

TABLE VIII

| Composition of the reaction medium | Vanillin obtained in mg/l | Yield |
| --- | --- | --- |
| Basic medium (reference) | 18 | 100% |
| Basic medium + cysteine (0.6 g) + gelatin (20 mg) + protoporphyrin IX (20 mg) + iron (0.125 mg) | 556 | 3088% |

Excellent results are again obtained here and the reactivity of eugenol with respect to cysteine is enhanced by the presence of gelatin, protoporphyrin IX and iron.

EXAMPLE 9

Preparation of Benzaldehyde

In a stirred reactor, a basic reaction medium is prepared to serve as a reference comprising:

2 l of borate buffer, 0.1M, pH 6.5

82 g of cinnamaldehyde and 1 g of Tween 80.

A reaction medium according to the invention is also prepared and comprises, apart from the basic reaction medium:

purified haemoglobin iron in the form of $FeCl_2$.

The reaction media are incubated at 30° C. for 48 hours in an agitated medium at 600 rpm, under a pressure of $10^4$ pascals of oxygen.

The results obtained are given in Table IX.

TABLE IX

| Composition of the reaction medium | Benzaldehyde in mg/l | Yield |
| --- | --- | --- |
| Basic medium (reference) | 500 | 100% |
| Basic medium + purified haemoglobin (2 g) + iron (10 mg) | 4220 | 844% |

Haemoglobin and iron increase spectacularly the yield of the oxidation reaction of cinnamaldehyde to benzaldehyde.

EXAMPLE 10

Preparation of Anisaldehyde

In a stirred reactor, a basic reaction medium is prepared to serve as a reference comprising:

2 l of borate buffer, 0.1M, pH 6.5

80 g of anethole and 1 g of Tween 80.

A reaction medium according to the invention is also prepared and comprises, apart from the basic reaction medium:

purified haemoglobin iron in the form of $FeCl_2$.

The reaction media are incubated at 30° C. for 48 hours in an agitated medium at 600 rpm, under a pressure of $10^4$ pascals of oxygen.

The results obtained are given in Table X.

TABLE X

| Composition of the reaction medium | Anisaldehyde in g/l | Yield |
| --- | --- | --- |
| Basic medium (reference) | 1.7 | 100% |
| Basic medium + purified haemoglobin (2 g) + iron (10 mg) | 14 | 823% |

Haemoglobin and iron increase spectacularly the yield of the oxidation reaction of anethole to anisaldehyde.

In EXAMPLES 11 to 13, the reaction conditions are the same as those outlined below.

In a stirred reactor, a basic reaction medium is prepared to serve as a reference comprising:

20 g of borate buffer, 0.1M, pH 6.5

800 mg of substrate, 50 mg of Tween 80.

A reaction medium according to the invention is also prepared and comprises, apart from the basic reaction medium:

purified haemoglobin or purified haemoglobin and iron in the form of $FeCl_2$.

The reaction media are incubated at 28° C. for 2 hours in an agitated medium at 150 rpm, under a pressure of $5.10^4$ pascals of oxygen. The results obtained are given in Tables XI to XIII.

EXAMPLE 11

Preparation of Vanillin

The substrate is isoeugenol

TABLE XI

| Composition of the reaction medium | Vanillin obtained in g/l | Yield |
|---|---|---|
| Basic medium (reference) | 0.42 | 100% |
| Basic medium + purified haemoglobin (20 mg) | 0.5 | 119% |
| Basic medium + purified haemoglobin (20 mg) + iron (0.1 mg) | 0.53 | 126% |

The effect of purified haemoglobin on the yield is clearly enhanced by the presence of iron.

EXAMPLE 12

Preparation of Anisaldehyde

The substrate is anethole.

TABLE XII

| Composition of the reaction medium | Vanillin obtained in g/l | Yield |
|---|---|---|
| Basic medium (reference) | 0.196 | 100% |
| Basic medium + purified haemoglobin (20 mg) | 0.188 | 96% |
| Basic medium + purified haemoglobin (20 mg) + iron (0.1 mg) | 0.244 | 124% |

We can but observe a fall (unexplained) in the yield in the case when purified haemoglobin is added to the basic medium, but the combination of purified haemoglobin-iron makes it possible to obtain a yield consistent with that obtained in the previous example.

EXAMPLE 13

Preparation of Benzaldehyde

The substrate is cinnamaldehyde.

TABLE XIII

| Composition of the reaction medium | Benzaldehyde obtained in g/l | Yield |
|---|---|---|
| Basic medium (reference) | 0.089 | 100% |
| Basic medium + purified haemoglobin (20 mg) | 0.809 | 909% |
| Basic medium + purified haemoglobin (20 mg) + iron (0.1 mg) | 0.833 | 936% |

Purified haemoglobin increases spectacularly the yield of the oxidation reaction of cinnamaldehyde to benzaldehyde, this reaction being particularly enhanced by the presence of iron.

EXAMPLE 14

Preparation of Vanillin

A basic reaction medium is prepared to serve as a reference comprising:
20 g of borate buffer, 0.1M, pH 6.5
800 mg of isoeugenol and
50 mg of Tween 80.

A reaction medium according to the invention is also prepared and comprises, apart from the basic reaction medium:
purified haemoglobin or
purified haemoglobin and iron in the form of $FeCl_2$.

The reaction media are incubated at 28° C. for 2 hours in an agitated medium at 150 rpm, under a pressure of $8.10^5$ pascals of oxygen.

The results obtained are summarised in Table XIV.

TABLE XIV

| Composition of the reaction medium | Vanillin obtained in g/l | Yield |
|---|---|---|
| Basic medium (reference) | 3 | 100% |
| Basic medium + purified haemoglobin (20 mg) | 3.57 | 119% |
| Basic medium + purified haemoglobin (20 mg) + iron (0.1 mg) | 5.69 | 190% |

The addition of iron to the basic medium in addition to purified haemoglobin enhances substantially the yield in which vanillin is obtained in comparison with the yield, already attractive, obtained in the case when the reaction medium consists only of the basic medium and purified haemoglobin.

We claim:

1. A process for the preparation of aromatic substances having the formula

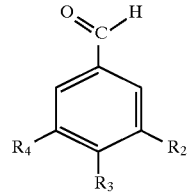

characterised in that a substrate corresponding to the formula

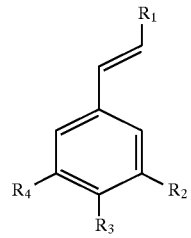

is subjected to oxidation,
a formula wherein
$R_1$ may be a radical —H, $CH_3$, —$CH_2OH$, —CHO, —COOH, —$OCH_3$ or —COO—CH(COOH)—$CH_2$—$C_6H_3(OH)_2$,
$R_2$ may be a radical —H, —OH, or —$OCH_3$,
$R_3$ may be a radical —H, —OH, —$OCH_3$, or 0-glucoside,
$R_4$ may be a radical —H, —OH, or —$OCH_3$,
said oxidation being carried out in the presence of at least one protein and of 0.0005 to 0.2% by weight with respect to the substrate of a metal ion which is in the free or complexed form and which is selected from the group consisting of iron, cobalt, copper, magnesium, manganese and zinc.

2. Process according to claim 1, characterised in that the glucoside in the radical $R_3$ is selected from the group consisting of glucopyranoside or glucopyranoside attached to an oside, said oside being selected from the group consisting of glucopyranoside, rhamnopyranoside, arabinopyranoside.

3. Process according to claim 1, characterised in that the aromatic substances are selected from the group consisting of vanillin, benzaldehyde, anisaldehyde, protocatechualdehyde.

4. Process according to claim 1, characterised in that the protein used is a metalloprotein.

5. Process according to claim 4, characterised in that the metalloprotein is selected from the group consisting of haemoglobin, myoglobin, and oxydoreductases.

6. Process according to claim 5, characterised in that the oxyreductase is selected from the group consisting of dehydrogenases and oxygenases.

7. Process according to claim 1, characterised in that the protein is selected from the group consisting of gelatin, casein, bovine serum albumin.

8. Process according to claim 1, characterised in that the protein is used in the purified form.

9. Process according to claim 1, characterised in that the protein is used in the unpurified form by means of a suspension of microbial cells, a ground preparation of cells, tissues or organs of vegetable or animal origin or of a protein preconcentrate of said compositions.

10. Process according to claim 1, characterised in that the protein is used in a quantity of 0.01 to 20% by weight with respect to the substrate.

11. Process according to claim 10, characterised in that the protein is used in a quantity of 0.1 to 5% by weight with respect to the substrate.

12. Process according to claim 1, characterised in that it is performed in water or in a buffered aqueous medium having a pH between 2 and 10.

13. Process according to claim 1, characterised in that it is performed at a temperature between 15° and 50° C.

14. Process according to claim 13, characterised in that it is performed at a temperature between 25° and 40° C.

15. Process according to claim 1, characterised in that it is performed at atmospheric pressure or under a pressure of air or oxygen between $10^3$ and $10^7$ Pascals.

16. Process according to claim 1, characterised in that it is performed under agitation.

17. Process according to claim 1, characterised in that it is performed for a period between 2 hours and 5 days.

18. Process according to claim 1, characterised in that the aromatic substances prepared are isolated from the reaction medium by extraction or by distillation.

* * * * *